(12) United States Patent
Breuille et al.

(10) Patent No.: US 12,059,016 B2
(45) Date of Patent: *Aug. 13, 2024

(54) COMPLEXES OF WHEY PROTEIN MICELLES AND PECTIN AND BODY MUSCLE PROTEIN SYNTHESIS

(71) Applicant: SOCIÉTÉ DES PRODUITS NESTLÉ S.A., Vevey (CH)

(72) Inventors: Denis Breuille, Lausanne (CH); Etienne Pouteau, Lausanne (CH); Simina Florentina Popa Nita, Morges (CH); Laurence Donato-Capel, Cheseaux sur Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 566 days.

This patent is subject to a terminal disclaimer.

(21) Appl. No.: 15/527,860

(22) PCT Filed: Nov. 9, 2015

(86) PCT No.: PCT/EP2015/076097
§ 371 (c)(1),
(2) Date: May 18, 2017

(87) PCT Pub. No.: WO2016/078956
PCT Pub. Date: May 26, 2016

(65) Prior Publication Data
US 2018/0343910 A1    Dec. 6, 2018

(51) Int. Cl.
| | | |
|---|---|---|
| A23L 33/19 | (2016.01) | |
| A23C 9/13 | (2006.01) | |
| A23K 20/147 | (2016.01) | |
| A23K 20/163 | (2016.01) | |
| A23L 33/00 | (2016.01) | |
| A23L 33/21 | (2016.01) | |
| A61K 35/20 | (2006.01) | |
| A61K 38/01 | (2006.01) | |

(52) U.S. Cl.
CPC ............ *A23L 33/19* (2016.08); *A23C 9/1307* (2013.01); *A23K 20/147* (2016.05); *A23K 20/163* (2016.05); *A23L 33/21* (2016.08); *A23L 33/30* (2016.08); *A23L 33/40* (2016.08); *A61K 35/20* (2013.01); *A61K 38/018* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| | | | |
|---|---|---|---|
| 6,355,612 B1 | 3/2002 | Ballevre et al. | |
| 6,423,354 B1 * | 7/2002 | Monte | A23C 11/04 426/321 |
| 6,475,539 B1 * | 11/2002 | DeWille | A23L 2/38 426/573 |
| 2006/0257548 A1 * | 11/2006 | Crofskey | A23C 9/1232 426/656 |
| 2007/0104849 A1 * | 5/2007 | McClements | A23L 2/385 426/590 |
| 2010/0047358 A1 * | 2/2010 | Pouzot | A61K 9/1272 424/498 |
| 2012/0156252 A1 * | 6/2012 | Brodkorb | A23L 11/34 424/400 |
| 2013/0065822 A1 * | 3/2013 | Miller | A61K 31/198 514/5.6 |
| 2019/0309258 A1 * | 10/2019 | Alcantar | C12N 5/0068 |

FOREIGN PATENT DOCUMENTS

| | | | | |
|---|---|---|---|---|
| EP | 1839492 A1 * | 10/2007 | | A23C 11/04 |
| WO | 2007073188 | 6/2007 | | |
| WO | WO-2007110411 A2 * | 10/2007 | | A23C 11/04 |
| WO | WO-2012081982 A2 * | 6/2012 | | A23J 3/08 |
| WO | WO-2013057230 A1 * | 4/2013 | | A61K 35/20 |

OTHER PUBLICATIONS

Wikipedia "Human body weight," last edited Feb. 8, 2019.*
Schmitt et al. "Internal structure and colloidal behavior of covalent whey protein microgels obtained by heat treatment," Soft Matter 6:4876-4884, 2010.*
Krzeminski et al. "Environmental response of pectin-stabilized whey protein aggregates," Food Hydrocolloids 35:332-340, 2014.*
Tuinier et al. "Electrosorption of pectin onto casein micelles," Biomacromolecules 3:632-638, 2002.*
Abbatecola et al. "Discovering pathways of sarcopenia in older adults: a role for insulin resistance on mitochondria dysfunction," The Journal of Nutrition, Health and Aging 15(10):890-895, 2011.*
Wikipedia "Gum arabic," last edited Oct. 8, 2019; https://en.wikipedia.org/wiki/Gum_arabic.*
Bengoechea et al. "Formation and characterization of lactoferrin/pectin electrostatic complexes: Impact of composition, pH and thermal treatment," Food Hydrocolloids 25:1227-1232, 2011 (Year: 2011).*
Souza et al. "Production and Characterization of microparticles containing pectin and whey proteins" Food Research International, 2012, vol. 49, pp. 560-566.

(Continued)

*Primary Examiner* — David J Blanchard
*Assistant Examiner* — Alissa Prosser
(74) *Attorney, Agent, or Firm* — K&L Gates LLP

(57) ABSTRACT

The present invention relates to the treatment or prevention of conditions linked to reduced muscle mass or reduced muscle protein synthesis rate. A subject matter of the invention is a composition comprising complexes of whey protein micelles and pectin for use in the treatment or prevention of a condition selected from the group consisting of sarcopenia, muscle atrophy and negative nitrogen balance. Further aspects of the invention relate to the non-therapeutic use of a composition comprising complexes of whey protein micelles and pectin and a food composition.

8 Claims, 2 Drawing Sheets

(56) References Cited

OTHER PUBLICATIONS

Lambers et al. "Fast and Slow Proteins: Modulation of the Gastric Behavior of Whey and Casein In Vitro" Food Dig., 2013, vol. 4, pp. 1-6.
Priority Document of EP Application No. 14193837.3, Filed on Nov. 19, 2014, 27 Pages.
Baccouche et al., "A Physical Stability Study of Whey-Based Prickly Pear Beverages", Food Hydrocolloids, vol. 33, Issue No. 2, 2013, pp. 234-244.
Zhang et al., "Intragastric Gelation of Whey Protein-Pectin Alters the Digestibility of Whey Protein During in Vitro Pepsin Digestion", Food and Function, vol. 5, Issue No. 1, 2014, pp. 102-110.
Oduse, "Whey Protein Concentrate and Pectin Complexes: Fabrication, Characterization and Applications", Heriot-Watt University, School of Life Sciences, Oct. 2015, 258 Pages.
EP Application No. 15790998.7, Filed on Nov. 9, 2015, 25 Pages.
Patent Proprietor's Submission for EP Application No. 15790998.7, Mailed on Dec. 27, 2017, pp. 1-6.

* cited by examiner

COMPLEXES OF WHEY PROTEIN MICELLES AND PECTIN AND BODY MUSCLE PROTEIN SYNTHESIS

CROSS REFERENCE TO RELATED APPLICATIONS

The present application is a National Stage of International Application No. PCT/EP2015/076097, filed on Nov. 9, 2015, which claims priority to European Patent Application No. 14193837.3 filed on Nov. 19, 2014, the entire contents of which are being incorporated herein by reference.

FIELD OF THE INVENTION

The present invention relates to the treatment or prevention of conditions linked to reduced muscle mass or reduced muscle protein synthesis rate. A subject matter of the invention is a composition comprising complexes of whey protein micelles and pectin for use in the treatment or prevention of a condition selected from the group consisting of sarcopenia, muscle atrophy and negative nitrogen balance. Further aspects of the invention relate to the non-therapeutic use of a composition comprising complexes of whey protein micelles and pectin and a food composition.

BACKGROUND OF THE INVENTION

The loss of muscle mass and muscle strength considerably decreases the quality of life of patients suffering from such a condition as they become unable to perform certain physical tasks and the risk of accidents related to such physical tasks like for example walking becomes increased. One may distinguish two major conditions which lead to a loss of muscle mass and strength, one being muscle atrophy and the other being sarcopenia. Disease associated muscle atrophy results from co-morbidity of several common diseases, including cancer, AIDS, congestive heart failure, chronic obstructive pulmonary disease and others. Disuse of the muscles from a lack of physical exercise for a longer period of time will also lead to muscle atrophy. Thereby, particularly bedridden patients can have significant muscle wasting. Moreover, starvation eventually leads to muscle atrophy as can be observed for example with overweight patients on a strict weight-loss diet.

Sarcopenia relates to the gradual decrease in the ability of maintaining muscle mass, function and strength which comes with age.

Loss of muscle mass occurs by a change in the normal balance between protein synthesis and protein degradation. During disease associated muscle atrophy, for example, there is a down-regulation of protein synthesis pathways, and an activation of protein breakdown pathways (Sandri M, 2008, Physiology 23:160-170). Since the absence of muscle-building amino acids, particularly of branched chain amino acids, can contribute to muscle wasting, the provision of sufficient amino acids can be helpful in regenerating damaged or atrophied muscle tissue. The branched chain amino acids (BCAAs), including leucine, isoleucine and valine, are critical in this process. Thereby, nutrition leading to a sustained hyper-aminoacidemia, i.e. an elevated concentration of amino acids in the plasma, especially of the BCAAs and further essential amino acids, is essential in stimulating muscle protein synthesis of a patient in need.

Previous studies demonstrated that an ingestion of a mixed meal typically stimulates skeletal muscle protein synthesis and that an adequate supply of amino acids is essential. Thereby, recent studies suggest that it is the supply of BCAAs and particularly of leucine, that modulate the protein synthetic response in skeletal muscle to meal feeding (Garlick P J et al., 1988, Biochem J 254:579-584; Anthony J C et al., 1999, J Nutr 129:1102-1106; Crozier Si et al., 2005, J Nutr 135:376-382). Further research indicated that the leucine content of a selected protein source of a meal is an important indicator of the protein quality as it relates to acute stimulation of muscle protein synthesis (Norton L E et al., 2009, J Nutr 139:1103-1109).

Tang J E et al. (2009, J Appl Physiol 107:987-992) investigated the response of skeletal muscle protein synthesis in young men following the ingestion of three distinct but high-quality dietary proteins, i.e. whey, micellar casein and soy, at rest and after resistance exercise. Thereby, it was reported that the consumption of whey proteins stimulated muscle protein synthesis to a greater degree than casein, both at rest and after resistance exercise. Whey proteins stimulated also a significantly larger rise in muscle synthesis than soy proteins, which was in congruence with previous work of the same authors. They concluded that whey proteins stimulate skeletal muscle protein synthesis to a greater extent than either casein or soy proteins, both at rest and after resistance exercise.

EP2583563 demonstrated that whey protein micelles may be used in the treatment or prevention of conditions linked to a reduced concentration of plasma amino acids in a patient, for example muscle atrophy or sarcopenia.

There is a persisting need to find better nutritional solutions for patients suffering from a loss of muscle mass or muscle strength. The object of the present invention is to improve the state of the art and to provide an improved nutritional solution to maintain an elevated concentration of plasma amino acids in a subject. The object of the present invention is achieved by the subject matter of the independent claims. The dependent claims further develop the idea of the present invention.

Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

Accordingly, the present invention provides in a first aspect a composition comprising complexes of whey protein micelles and pectin for use in the treatment or prevention of a condition selected from the group consisting of sarcopenia, muscle atrophy and negative nitrogen balance, wherein the weight ratio of whey protein micelles to pectin in the composition is between 30:1 and 0.8:1.

In a second aspect, the invention relates to the non-therapeutic use of a composition comprising complexes of whey protein micelles and pectin to maintain weight in elderly subjects, wherein the weight ratio of whey protein micelles to pectin in the composition is between 30:1 and 0.8:1.

A further aspect of the invention relates to a food composition comprising complexes of whey protein micelles and pectin wherein the weight ratio of whey protein micelles to pectin in the composition is between 30:1 and 0.8:1

"Whey protein micelles" (WPM) are defined herein as described in EP1839492A1 and as further characterized in Schmitt C et al. [Soft Matter 6:4876-4884 (2010)], where they are referred to as whey protein microgels (WPM). Particularly, the "whey protein micelles" are the micelles comprised in the whey protein micelles concentrate obtainable by the process as disclosed in EP1839492A1. Therein, the process for the production of whey protein micelles concentrate comprises the steps of: a) adjusting the pH of a whey protein aqueous solution to a value between 3.0 and 8.0; b) subjecting the aqueous solution to a temperature between 80 and 98° C.; and c) concentrating the dispersion obtained in step b). Thereby, the micelles produced have an extremely sharp size distribution, such that more than 80% of the micelles produced have a size smaller than 1 micron in diameter and preferably are between 100 nm and 900 nm in size. The "whey protein micelles" can be in liquid concentrate or in powder form. Importantly, the basic micelle structure of the whey proteins is conserved, in the concentrate, the powder and reconstituted from the powder for example in water. The "whey protein micelles" are physically stable in dispersion, as powder as well as during spray-drying or freeze-drying.

A rapid increase in plasma amino acids is required for stimulating muscle protein synthesis at rest and after exercise [Dangin M et al., 2003, J Physiol 549:635-644]. Such an increase in plasma amino acids can be provided for example by whey protein isolate (WPI) [Tang J E et al., 2009, J Appl Physiol 107:987-992]. A more sustained amino acid response may prolong the anabolism and increase muscle protein synthesis by providing amino acid building blocks over a longer period of time [Lacroix M et al., 2006: Am J Clin Nutr 84:107-9]. In addition, a more slowly digested protein may suppress protein breakdown [Dangin M et al., 2001, Am J Physiol 280:E340-E348], which would have an additional benefit for the net muscle protein balance, i.e. the difference between protein synthesis and protein breakdown. Thus, a protein or a mix of proteins that would induce the maximal aminoacidemia but during a longer period of time would do both, i.e. maximally stimulate protein synthesis and suppress protein breakdown.

The stimulation of muscle protein synthesis rate, the building of muscle protein and the positive nitrogen balance are linked to an increased concentration of amino acids associated with a meal or a dietary supplement. This anabolic process is therefore directly related to the increase concentration of amino acids and it is recognized that in condition of disease or in elderly subjects, an anabolic resistance to this stimulation is present meaning that the increase in plasma amino acids needs to be higher than in young subjects to get the same stimulation. Thus the higher is the amino peak and the longer it will be, the higher will be also the stimulation of muscle protein synthesis.

It has now been surprisingly found by the inventors that consumption of a composition comprising complexes of whey protein micelles (WPM) and pectin by minipigs induces a more sustained amino acid absorption than consumption of an iso-caloric and iso-nitrogenous control composition with just whey protein micelles. The results of the pre-clinical study are presented in the Examples section.

Hence, the inventors have found a composition which induces a sustained but high maximal aminoacidemia in a subject. This hyper-aminoacidemia for a prolonged postprandial period of time is most favourable for maximally stimulating muscle protein synthesis, reducing protein breakdown and therefore maintaining or even enhancing muscle mass.

An excess of amino acids in the bloodstream (hyperaminoacidemia) can lead to an increase in protein synthesis and reduction of protein breakdown with an overall positive nitrogen balance. This positive nitrogen balance reflects more construction of lean tissue than destruction, leading overall to an increase in lean body mass.

Although not wishing to be bound by theory, the inventors think that whey protein micelles complexed with pectin induce a delayed gastric emptying or are more slowly digested than whey protein micelles alone. Thereby, complexes of whey protein micelles and pectin deliver the amino acids more slowly into the peripheral blood circulation.

DETAILED DESCRIPTION OF THE INVENTION

Figure 1:
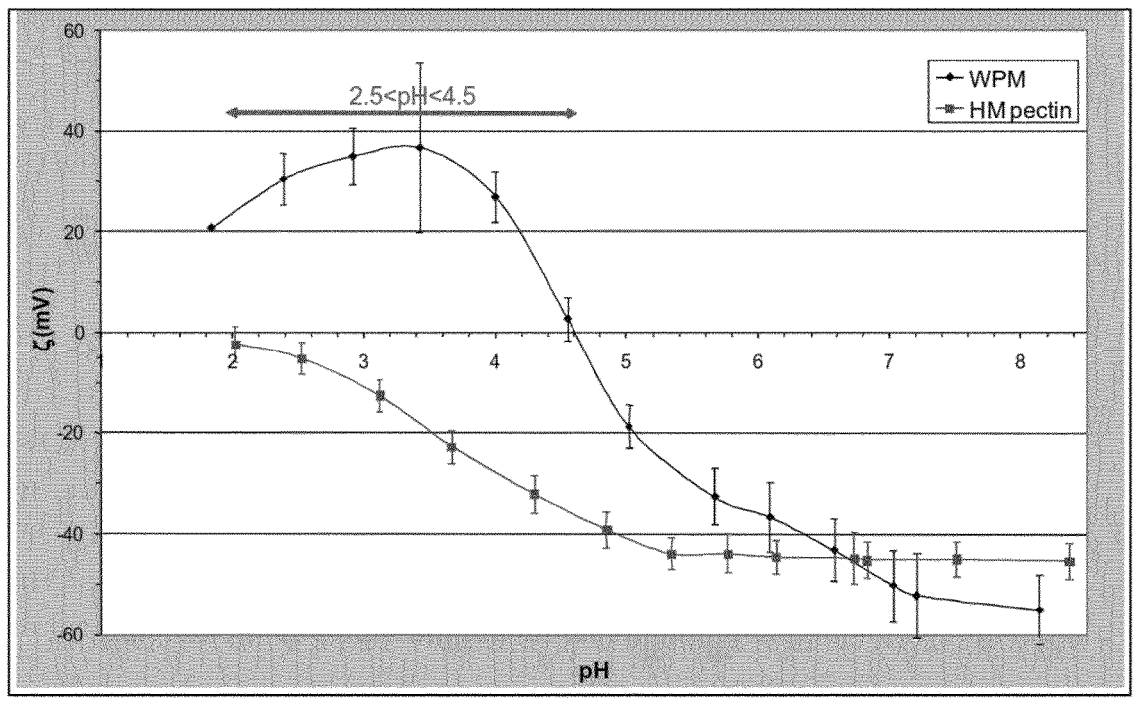
FIG. 1: Variation of surface charge ($\zeta$-potential) as a function of pH for WPM and pectin in solutions of concentration 0.1 wt % and at T=25° C.

The present invention relates to a composition comprising complexes of whey protein micelles and pectin for use in the treatment or prevention of a condition linked to a reduced muscle mass or reduced muscle synthesis rate. In particular the invention provides a composition comprising complexes of whey protein micelles and pectin, for example electrostatic complexes, for use in the treatment or prevention of a condition selected from the group consisting of sarcopenia, muscle atrophy and negative nitrogen balance, wherein the weight ratio of whey protein micelles to pectin in the composition is between 30:1 and 0.8:1, for example between 10:1 and 1:1. The whey protein micelles in the composition of the invention may be obtainable (for example obtained) by adjusting the pH of a whey protein aqueous solution to a value between 3.0 and 8.0 and subjecting the aqueous solution to a temperature between 80 and 98° C. For example, the whey protein micelles in the composition of the invention may be obtainable (for example obtained) by adjusting the pH of a demineralized native whey protein aqueous solution to a value between 5.8 and 6.6 and subjecting the aqueous solution to a temperature between 80 and 98° C. for a period of between 10 seconds and 2 hours.

The invention may relate to the use of a composition comprising complexes of whey protein micelles and pectin for the manufacture of a medicament for use in the treatment or prevention of a condition selected from the group consisting of sarcopenia, muscle atrophy and negative nitrogen balance, wherein the weight ratio of whey protein micelles to pectin in the composition is between 30:1 and 0.8:1.

As the ratio of WPM to pectin increases above 30:1, the beneficial effect of the complexes becomes indistinguishable to WPM alone. For example, a minimum of 0.1% of the overall composition may be pectin on a dry weight basis, for further example a minimum of 2% of the overall composition may be pectin on a dry weight basis. The pectin may be high methyl-esterified pectin. For ratios of WPM to pectin below 0.8:1, the compositions cannot provide sufficient protein to affect the plasma amino acids without becoming unacceptably viscous. The weight ratio of whey protein micelles to pectin in the complexes comprised within the composition of the invention may be between 30:1 and 0.8:1, for example between 10:1 and 1:1. The hyper-aminoacidemia for a sustained postprandial period of time provided by the inventive use of the complexes of whey protein micelles and pectin is most favourable for maximally stimulating muscle protein synthesis and therefore maintaining or even enhancing muscle mass.

Compositions comprising complexes of whey protein micelles and pectin may for example be formed by combining an aqueous dispersion of pectin with an aqueous dispersion of whey protein micelles at a pH of between 2.5 and 4.5. The pH of the dispersions may be such that the final pH is in this range directly, or the pH may be adjusted to be within this range after combining the dispersions. The complexes may be used in the form of an aqueous dispersion, or they may be dried, for example to be used as a powder.

Sarcopenia and muscle atrophy are components of physical frailty, a common geriatric syndrome. The present invention is adapted to provide a nutritional solution to patients suffering from these conditions, to reduce or stop loss of muscle mass and/or ultimately to build up again muscle mass and strength.

The composition of the invention may be for use in the treatment or prevention of sarcopenia. "Sarcopenia" is defined as the degenerative loss of muscle mass and function (including strength) associated with aging. Sarcopenia is characterized first by a decrease in the size of the muscle, which causes weakness and frailty. However, this loss of muscle mass may be caused by different cellular mechanisms than those that cause muscle atrophy due to a specific disease. For example, during sarcopenia, there is a replacement of muscle fibres with fat and an increase in fibrosis.

The composition of the invention may be for use in the treatment or prevention of muscle atrophy. "Muscle atrophy" is defined as a decrease in the mass of muscles in a subject. It can be a partial or complete wasting away of muscle tissue. When a muscle atrophies, this leads to muscle weakness, since the ability to exert force is related to muscle mass. Muscle atrophy results from a co-morbidity of several common diseases, including cancer, AIDS, congestive heart failure and chronic obstructive pulmonary disease. Moreover, starvation eventually leads to muscle atrophy. Disuse of the muscles will also lead to atrophy.

The composition of the invention may be for use in the treatment or prevention of negative nitrogen balance. A negative nitrogen balance occurs when the amount of nitrogen excreted from the body is greater than the amount of nitrogen ingested, so there is a decrease in the total body pool of protein. A negative nitrogen balance can be associated with burns, fevers, wasting diseases and other serious injuries and during periods of fasting.

The composition for use according to the invention may be administered to a critically ill patient, a patient after surgery, a trauma patient, a cancer patient, or a patient during and after bed rest. The common fate of all these patients is that they are dramatically losing muscle mass and/or are at risk of dramatically losing (even further) muscle mass. Hence, it is those patients that would maximally profit from the new current invention.

A "critically ill patient" is defined as a patient who is at high risk for an actual or potential life-threatening health problem. The more critically ill the patient is the more likely he or she is to be highly vulnerable, unstable and complex, thereby requiring intense and vigilant nursing care.

A "trauma patient" is a person who has suffered a trauma. Thereby, trauma refers to a body wound or shock produced by sudden physical injury, as for example from violence or an accident. People who have suffered trauma usually require specialized care.

A "cancer patient" is a patient who has cancer.

Disuse atrophy may occur in patients who lack of physical exercise such as patients during and after bed rest. The muscle atrophy being caused by the patient not using their muscles enough.

The composition for use according to the invention may be administered in combination with a meal. Most meals comprise proteins from a milk, plant and/or animal source and hence upon consumption lead to a postprandial aminoacidemia increase, i.e. an elevated concentration of amino acids in the plasma of the consumer. It is an advantage to combine the administration of WPM/pectin complexes with such a meal. Thereby, the postprandial plasma amino acid levels resulting from the proteins present in the meal are combined with the sustained postprandial amino acid levels resulting from the WPM/pectin complexes. Thereby, the overall resulting hyper-aminoacidemia is extended and prolonged in time. This in return is most favourable for maximally stimulating muscle protein synthesis, reducing muscle protein breakdown and therefore maintaining or even enhancing muscle mass.

The meal may comprise whey protein isolates, native or hydrolyzed milk proteins, free amino acids, or a combination thereof. As known from earlier studies, a whey protein meal exhibits a significantly stronger aminoacidemia effect on subjects than for example a plant protein meal. Therefore, advantageously, the WPM/pectin complexes are combined with a meal comprising whey proteins in the form of WPI or milk. Advantageously, the meal can be even further supplemented with free amino acids in combination with the whey or milk proteins to optimally induce a hyper-aminoacidemia upon consumption of said meal.

The composition for use according to the invention may be administered to a patient during the period of at least one day before surgery and/or hospital stay to at least one week after surgery and/or hospital stay. Thereby, advantageously, a patient builds up his plasma amino acid pool already before undergoing surgery or a longer bedridden hospital stay and continues to maintaining such an elevated concentration of the essential amino acids during the full period of recovery. This provides him with an optimal nutritional status to minimize loss of muscle mass during the hospital intervention and also prepares him for a quicker recovery and build-up of lost muscle tissues thereafter.

The composition may be administered in a daily dose to provide between 0.1 g and 2.0 g dry weight of whey protein micelles per 1 kg body weight, for example between 0.2 g and 1.5 g dry weight of whey protein micelles per 1 kg body weight. The composition may be administered in a daily dose to provide between 0.1 g and 3.5 g dry weight of complexes of whey protein micelles and pectin per 1 kg body weight, for example between 0.2 g and 2.5 g dry weight of complexes of whey protein micelles and pectin per 1 kg body weight. Those doses should assure a sufficient daily quantity for providing the desired effect to a subject in at least a mid-term period.

The composition may be in any convenient form, for example the composition may be in the form of a beverage, nutritional composition, bar, flakes or as pellets. The composition may be an oral nutritional support.

The composition may be a heat treated. An important method of controlling food hygiene risks is to heat treat edible compositions which may harbour food pathogens or spoilage organisms. Well-known examples of such heat treatments are pasteurization, for example heating an edible material to 72° C. for 15 seconds, and ultra-high temperature (UHT) treatment, for example heating an edible material to above 135° C. for at least 2 seconds. Heat treatment may be critical when the composition is to be administered to a subject with a weakened immunity to infection such as an elderly person or a patient in hospital.

The composition may be a heat treated liquid. Generally, the protein content that can be included in heat sterilized liquid compositions is greatly limited. Compositions with high contents of protein form thick gels on heating and so do not provide a convenient liquid format once heat treated. For example a native whey protein dispersion forms a gel in the presence of 0.1 M of sodium chloride at a protein concentration of only 4 wt. % after a heat treatment 85° C. for 15 min. The addition of pectin would be expected to make the problem of gelling worse. For example, the addition of pectin to whey protein has been found to decrease the protein gelling concentration or the gel time upon heat treatment [S. L. Turgeon et al., Food Hydrocolloids, 15, 583-591 (2001)]. The surprising finding that liquid compositions comprising WPM/pectin complexes may be heat treated and still remain liquid therefore allows an advantageous liquid composition to be provided. The heat treated liquid composition for use according to the invention may have a total content of whey protein micelles of at least 5 wt. %, for example at least 10 wt. %.

The liquid composition for use according to the invention may be a liquid meal replacement. Whey protein micelles have a more "milky" appearance compared to whey protein isolates. This can enhance the appearance of liquid drinks or meal replacers. The liquid meal replacement may be in a form suitable for enteral tube feeding. Thereby, advantageously, such a meal replacement can for example be used in intensive care units or hospitals, where patients due e.g. to their trauma require a high protein diet for recovery. A liquid meal replacement thereby is very convenient and provides the required amounts of proteins in a well-adapted formulation. Enteral tube feeding is a way to provide food or nutrition through a tube placed in the nose, the stomach or the small intestine. Enteral tube feeding is often also called enteral nutrition. The liquid composition may further comprise lipids and carbohydrates to provide appropriate nutrition. The liquid composition permits a large quantity of protein to be delivered in a relatively small volume without bad taste or texture. This confers a significant advantage and originality for the production of liquid meal replacers and meal replacement systems. It allows to provide liquid meal replacement products with high amounts of whey proteins.

The total content of whey protein micelles in the composition for use according to the invention may be at least 5 wt. %, for example at least 10 wt. % on a dry weight basis. The total content of complexes of whey protein micelles and pectin in the composition for use according to the invention may be at least 5 wt. %, for example at least 10 wt. %.

As discussed above, it is of an advantage to combine the administration of WPM/pectin complexes with whey proteins in the form of WPI, milk and/or even free amino acids to optimally induce and extend a hyper-aminoacidemia upon consumption of such a meal. Preferably, the different protein components are combined together into one meal replacement product or kit of products. Thereby, the individual protein components can be optimally dosed for providing a best and prolonged hyper-aminoacidemia effect and at the same time optimized for a good, organoleptically best acceptable product application.

A further aspect of the present invention is the non-therapeutic use of a composition comprising complexes of whey protein micelles and pectin to maintain weight, increase muscle mass or increase muscle strength wherein the weight ratio of whey protein micelles to pectin in the composition is between 30:1 and 0.8:1, for example between 10:1 and 1:1. The whey protein micelles in the composition used according to the invention may be obtainable (for example obtained) by adjusting the pH of a whey protein aqueous solution to a value between 3.0 and 8.0 and subjecting the aqueous solution to a temperature between 80 and 98° C. For example, the whey protein micelles in the composition used according to the invention may be obtainable (for example obtained) by adjusting the pH of a demineralized native whey protein aqueous solution to a value between 5.8 and 6.6 and subjecting the aqueous solution to a temperature between 80 and 98° C. for a period of between 10 seconds and 2 hours.

Healthy individuals may wish to maintain a constant body weight, for example healthy elderly subjects (such as human beings and animals) who have smaller appetites than when they were younger and for whom it would be beneficial to ensure proper muscle protein synthesis. People preparing for or ending a period of fasting, for example for reasons of religious observance, may benefit from consuming a composition that provides a sustained level of amino acids in the blood and helps maintain optimal nutritional status and body weight. Such a composition is provided by the composition according to the non-therapeutic use of the invention. Athletes and body-builders may also wish to consume compositions that increase their muscle mass or increase their muscle strength.

A subject is considered as "elderly" if they have surpassed the first two thirds of their average expected lifespan in their country of origin, preferably if they have surpassed the first three quarters of the average expected lifespan in their country of origin, more preferably if they have surpassed the first four fifths of the average expected lifespan in their country of origin. For example, a human male born in the UK in 2010 has a life expectancy at birth of 78 years according to the UK Office of National Statistics, therefore they would be considered elderly at ages over 52 years, preferably over 58 years 6 months and more preferably over 62 years 5 months. For pets and livestock the species and breed should be taken into account. For example a Yorkshire Terrier dog has a life expectancy of about 12 years [E. J. Taylor et al., Proceedings of the Nutrition Society, 54, 645-656 (1995)] and so would be considered elderly at ages over 8 years, preferably over 9 years and more preferably over 9 years 7 months.

It is an advantage of the present invention that a composition comprising complexes of whey protein micelles and pectin can also be administered to elderly subjects, for example healthy elderly subjects, which may be at risk of losing weight, especially muscle mass at some later time. WPM/pectin complexes as disclosed herein may provide healthy elderly subjects with high quality protein and sustained plasma amino acid levels and so can improve the general health status of those subjects.

In a further aspect, the invention provides a food composition, for example to be administered to an elderly subject, comprising complexes of whey protein micelles and pectin wherein the weight ratio of whey protein micelles to pectin in the composition is between 30:1 and 0.8:1, for example between 10:1 and 1:1. The whey protein micelles in the food composition of the invention may be obtainable (for example obtained) by adjusting the pH of a whey protein aqueous solution to a value between 3.0 and 8.0 and subjecting the aqueous solution to a temperature between 80 and 98° C. For example, the whey protein micelles in the food composition of the invention may be obtainable (for example obtained) by adjusting the pH of a demineralized native whey protein aqueous solution to a value between 5.8 and 6.6 and subjecting the aqueous solution to a temperature between 80 and 98° C. for a period of between 10 seconds and 2 hours.

The total content of whey protein micelles in the food composition of the invention may be at least 5 wt. %, for example at least 10 wt. %. The total content of complexes of whey protein micelles and pectin in the food composition of the invention may be at least 5 wt. %, for example at least 10 wt. %. The food composition of the invention may comprise 5-20 wt. % proteins, 1-15 wt. % lipids, 25-50 wt. % carbohydrates and 0.1-10 wt. % fibres of total dry weight.

The food composition of the invention may be a fermented milk product such as a yoghurt, for example a spoon-able yoghurt, a drinking yoghurt or a strained yoghurt. In the context of the present invention the term yoghurt may include, but is not limited to, materials complying with local food labelling regulations concerning the term "yoghurt". Yoghurts are a convenient product format for providing a source of protein, having good consumer acceptance. The WPM/pectin complexes increase viscosity when added to a liquid product, which is generally desirable in yoghurt. The food composition of the invention may be a meal replacement or an oral nutritional supplement. The food composition of the invention may be a pet food. Pets such as dogs may show muscle loss as they age and so it is beneficial to be able to provide a food composition for pets which can help to prevent loss of muscle mass.

Those skilled in the art will understand that they can freely combine all features of the present invention disclosed herein. In particular, features described for the composition for therapeutic use may be used and combined with the features of the non-therapeutic use and/or the food composition, and vice versa. Further, features described for different embodiments of the present invention may be combined. Further advantages and features of the present invention are apparent from the figures and examples.

EXAMPLES

Example 1

Preparation of Pectin-Whey Protein Micelles Complexes

Whey protein micelle powder (WPM) was produced by heat treatment at 85° C./15 min of a dispersion of whey protein isolate (Prolacta 90) at 4% wt protein at pH 5.89, then concentration by microfiltration up to 22% wt total solid and spray drying.

A pectin (high methyl-esterified pectin, Classic CU201, Herbstreith & Fox K G) stock solution of 5 wt. % was prepared in de-ionised water by stirring for 2-3 hours at 60° C. To allow complete hydration of the chains, the solution was stirred overnight at 4° C. A WPM stock solution of 15% wt and pH 3.5 was prepared. Firstly, the powder was dispersed in a 135 mM HCl solution, overnight at 4° C. The dispersion was then homogenized at 250 bars, 2 passes and at 50 bars, 1 pass. The final dry matter and subsequent protein concentration were verified using a HR73 Halogen Moisture Analyzer (Mettler Toledo) and the particle size was checked by dynamic light scattering (Zetasizer Nanoseries, Malvern, UK). Typical values were: hydrodynamic diameter $Dh=300$ nm, polydispersity index pdI=0.15. Mixes of different protein concentrations (range 0.1-10 wt %) and WPM/pectin weight ratios (range 1:1-10:1) were obtained by blending the two solutions (and adding water if necessary). The mix was then homogenized at 500 bars for 2 passes at 25° C. Final pH of the system was adjusted to pH 4.0 using 1M NaOH.

Physicochemical Characterization of the Systems:

Surface Charge

The surface charge corresponding to the electrophoretic mobility, the $\zeta$-potential, of the particles was measured with a particle mobility distribution instrument (Zetasizer Nanoseries, Malvern, UK). A multipurpose titrator unit (MPT 2, Malvern) with 1M HCl and NaOH titrant solutions was used to vary the pH from 8 to 2 with an increment of 0.5 and a pH precision target of 0.3. A cell DTS1060C was used and the measurements were done at 25° C. 15 mL of 0.1% wt solution was employed. The data processing was done automatically.

Particle Size Distribution

Particle size distribution was measured using multi-angle static light scattering with a Mastersizer S long bench (Malvern, UK). Refractive indices of 1.36 for the disperse phase and 1.33 for the continuous phase and a backscattering index of 0.1 (3JHD presentation) were used in the calculation. Residual values were always lower than 1.5. Taking into account the arbitrary choice of the refractive index of the disperse phase and the mathematical model used (which assumes particles are spherical), present measurements only provide a qualitative indication of the aggregation in the systems rather than a quantitative determination of particle sizes.

Results

I. Identification of pH Conditions Allowing Formation of WPM/Pectin Electrostatic Complexes The surface charge ($\zeta$-potential) of WPM and pectin as function of pH is illustrated in FIG. 1. As pH increased from 2 to 8, the $\zeta$-potential of pectin decreased from neutral to $-45$ mV. This variation can be related to the carboxyl groups on the pectin backbone, At low pH, the neutralization of these groups induced $\zeta$-potential values close to zero. For WPM, the $\zeta$-potential varied from 20 mV at pH 2 to 40 mV at pH 3.8 and decreased to $-45$ mV at pH 8 with electroneutrality measured at pH 4.6. The latter can be related to the isoelectric point of $\beta$-lactoglobulin, the main constitutive protein of the WPM.

These results showed that in the pH range 2.5-4.5 the two components carried opposite charges and thus, are susceptible to forming electrostatic complexes.

II. Particle Size Distribution

Figure 2:
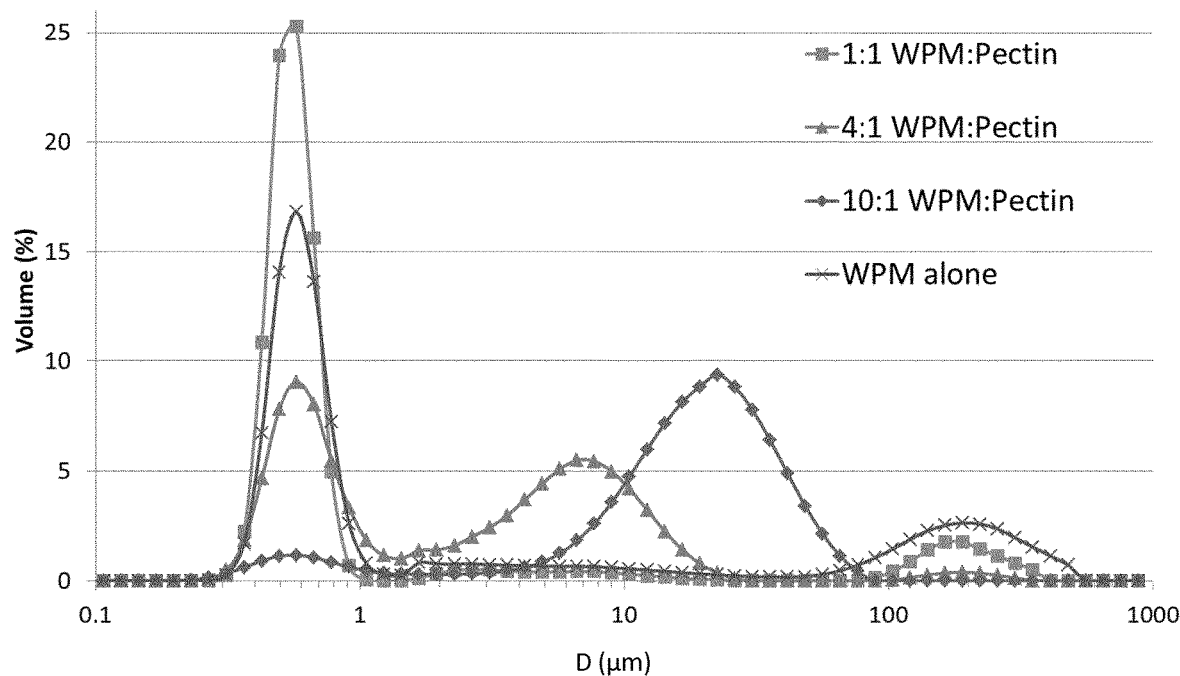
FIG. 2: Particle size distribution in WPM/pectin systems (at pH=4) of protein concentration of 1 wt % and different pectin concentrations (weight ratios WPM:pectin between 1:1 and 10:1). Results are presented as scattered light intensity versus particle diameter in volume.
Figure 3:
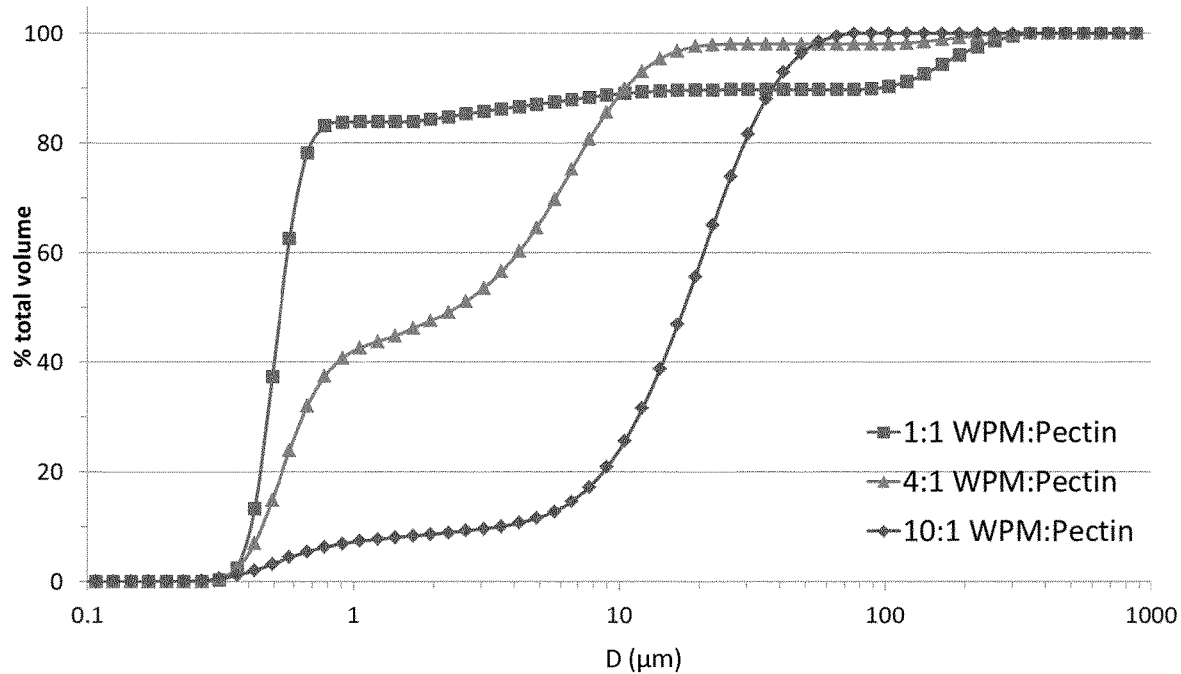
FIG. 3: Particle size distribution in WPM/pectin systems (at pH=4) of protein concentration of 1 wt % and different pectin concentrations (weight ratios WPM:pectin between 1:1 and 10:1). Results are presented as percentage of total volume versus particle diameter.

In order to evaluate the variations induced by pectin addition to WPM, particle size distribution was measured and FIGS. 2 and 3 present the results obtained for systems containing 1 wt % WPM and increasing amounts of pectin, from 0.1 wt % to 1 wt %, corresponding to WPM:pectin weight ratios of 10:1 to 1:1.

At low pectin concentration (0.1 wt %), the mean diameter of the particles was higher than 10 μm and less than 10% of the total sample volume was represented by particles with diameters lower than 1 μm. As the pectin concentration increased up to 1 wt %, the mean diameter decreased below 1 μm and more than 80% of the total volume was represented by particles with diameters lower than 1 μm. At pectin concentration of 1 wt %, the average size of the particles was comparable to WPM alone. For high WPM: pectin ratios (i.e. low pectin concentrations), interactions between WPM and pectin are likely to occur due to charge effect and large aggregates are mainly formed. As pectin concentration increases, complexes comparable in size with WPM are formed probably due to compaction of pectin chains at the surface of the WPM.

The results show that an aqueous dispersion of pectin and whey protein micelles will form pectin-whey protein micelle complexes at pH conditions between 2.5 and 4.5.

Example 2

Influence of Complexes of Whey Protein Micelles and Pectin on Amino Acid Appearance The inventors monitored the postprandial response of plasma amino acid concentration in a randomized double-blinded crossover study in healthy minipigs. A wash-out period of at least 6 days was kept between two meals and during this time, minipigs were given regular diet.

The following iso-caloric and iso-nitrogenous meal replacements were compared.

| | |
|---|---|
| A | Whey protein micelles (WPM) + lipids + maltodextrin |
| B | WPM/pectin complexes + lipids + maltodextrin |

Both meals were approximately 300 ml and contained 30 g of whey protein, 11 g of lipid and 30 g of maltodextrin. Meal B also contained 1.5 g pectin (high methyl-esterified pectin, Classic CU201, Herbstreith & Fox K G). The calorific value and protein content were measured analytically and the size of each test meal slightly adjusted to ensure they were all iso-caloric and iso-nitrogenous. Meal A was at neutral pH and Meal B was at acidic pH.

Meal A: WPM powder was produced by heat treating a 4 wt. % protein dispersion (pH 5.89) of WPI (Prolacta 90) at 85° C. for 15 minutes, then concentration by microfiltration up to 22 wt. % solids and spray drying. A 15% t.s. solution (pH 7) of WPM was homogenised and mixed with a homogenised emulsion of 40% oil in water stabilized by 4% Citrem emulsifier. Maltodextrin (DE 21) was added, and the mixture underwent UHT treatment at 148° C. for 3 seconds before filling into sterile bottles.

Meal B: WPM powder was produced as for meal A. A 15% t.s. solution (pH 4) of WPM was homogenised and mixed with pectin and maltodextrin at 60° C. for 1 hour to form WPM/pectin complexes. The mixture was then homogenized at 250 bar and mixed with a homogenised emulsion of 40% oil in water stabilized by 4% Citrem emulsifier. The pH was checked/adjusted to be pH 4. The mixture underwent UHT treatment at 148° C. for 3 seconds before filling into sterile bottles.

Figure 4:
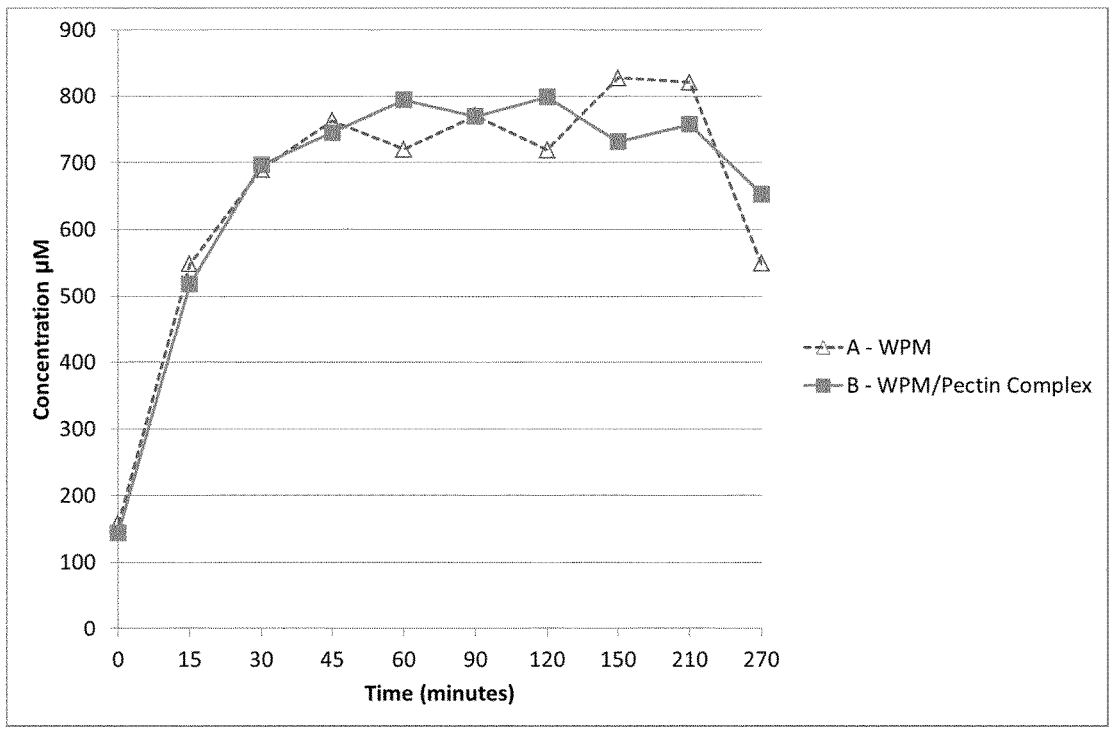
FIG. 4: Leucine concentration in plasma ($\mu$M) versus time after meal for WPM (A) and WPM/pectin complexes (B).

Blood samples were taken at 11 time points from 30 minutes before the meal to 270 minutes after, and the plasma leucine concentration determined. The results are plotted in FIG. 4. The areas under the two curves are essentially the same, showing that the overall leucine delivered was the same. However, it can be seen that while the concentration of leucine starts to tail-off between 210 and 270 minutes for sample A (WPM), the leucine concentration remains higher for sample B (WPM/pectin) demonstrating a more sustained amino acid absorption. This study showed the advantage of compositions comprising WPM/pectin complexes for maintaining an elevated concentration of plasma amino acids in a subject.

The invention claimed is:

1. A method for treatment or prevention of a condition selected from the group consisting of sarcopenia, muscle atrophy and negative nitrogen balance in a subject in need thereof by maintaining an elevated concentration of plasma amino acids in the subject, the method comprising:
   adjusting the pH of a whey protein aqueous solution to a value between 5.8 and 6.6 and subjecting the whey protein aqueous solution to a temperature between 80° C. and 98° C. for a period between 10 seconds and 2 hours to form whey protein micelles;
   forming electrostatic complexes of the whey protein micelles and pectin by combining an aqueous dispersion of the pectin with an aqueous dispersion of the whey protein micelles at a pH between 2.5 and 3.5; and
   providing to the subject a composition comprising the electrostatic complexes of the whey protein micelles and the pectin effective in inducing a sustained amino acid absorption, in a daily dose comprising between 0.1 g and 2.0 g dry weight of the whey protein micelles per 1 kg body weight of the subject,
   wherein the weight ratio of the whey protein micelles to the pectin in the composition is between 10:1 and 1:1.

2. The method according to claim 1, wherein the subject is selected from the group consisting of a critically ill patient, a patient after surgery, a trauma patient, a cancer patient, a patient during bed rest, a patient after bed rest, and combinations thereof.

3. The method according to claim 1, wherein the composition is provided in combination with a meal.

4. The method according to claim 1, wherein the composition is provided to the subject during the period from at least one day before surgery and/or hospital stay to at least one week after the surgery and/or the hospital stay.

5. The method according to claim 1, wherein the composition is subjected to an additional heat treatment and remains a liquid.

6. The method according to claim 1, wherein the composition is a liquid meal replacement.

7. The method according to claim 6, wherein the liquid meal replacement is in a form suitable for enteral tube feeding.

8. The method according to claim 1, wherein the total content of the whey protein micelles in the composition is at least 5 wt. %.

* * * * *